(12) United States Patent
Yada et al.

(10) Patent No.: US 7,067,695 B2
(45) Date of Patent: Jun. 27, 2006

(54) METHOD OF VAPOR PHASE CATALYTIC OXIDATION USING MULTITUBULAR REACTOR

(75) Inventors: Shuhei Yada, Yokkaichi (JP);
Hirochika Hosaka, Tokyo (JP);
Kimikatsu Jinno, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/064,020

(22) Filed: Feb. 23, 2005

(65) Prior Publication Data

US 2005/0148793 A1 Jul. 7, 2005

Related U.S. Application Data

(63) Continuation of application No. PCT/JP03/10600, filed on Aug. 21, 2003.

(30) Foreign Application Priority Data

Aug. 23, 2002 (JP) ............................. 2002-243402

(51) Int. Cl.
*C07C 51/21* (2006.01)
(52) U.S. Cl. ..................................... 562/545

(58) Field of Classification Search .................. None
See application file for complete search history.

(56) References Cited

FOREIGN PATENT DOCUMENTS

| EP | 1 080 781 | 3/2001 |
|----|-----------|--------|
| JP | 58-67335 | 4/1983 |
| JP | 08-92147 | 4/1996 |
| JP | 11-189555 | 7/1999 |
| JP | 11-199524 | 7/1999 |
| JP | 200-93784 | 4/2000 |
| JP | 2001-137689 | 5/2001 |

*Primary Examiner*—Paul A. Zucker
(74) *Attorney, Agent, or Firm*—Wenderoth, Lind & Ponack, L.L.P.

(57) ABSTRACT

An object of the present invention is to provide a method of vapor phase catalytic oxidation which is capable of: efficiently removing heat of reaction; preventing the formation of hot spots; and efficiently providing a desired product. The invention provides a method of vapor phase catalytic oxidation of a substance to be oxidized with a gas containing molecular oxygen by means of a multitubular reactor, wherein the method comprises: performing a reaction of vapor phase catalytic oxidation under such conditions that a heat transfer coefficient of the heat medium is $1,000$ $W/(m^2 \cdot K)$ or higher.

2 Claims, 5 Drawing Sheets

METHOD OF VAPOR PHASE CATALYTIC OXIDATION USING MULTITUBULAR REACTOR

This application is a Continuation application of PCT/JP2003/010600, filed Aug. 21, 2003.

TECHNICAL FIELD

The present invention relates to a method of vapor phase catalytic oxidation. The present invention is preferably used for oxidizing propylene, propane, or isobutylene with molecular oxygen to efficiently produce (meth)acrolein or (meth)acrylic acid.

BACKGROUND ART

A multitubular reactor is used for a reaction in which a raw material is brought into contact with a solid catalyst loaded in the reactor. The multitubular reactor controls the reaction temperature by efficiently removing large heat of reaction generated from a reaction of vapor phase catalytic oxidation in which a substance to be oxidized is brought into contact with molecular oxygen in the presence of a solid catalyst. In general, the reactor is used when there is a need for preventing the deterioration of the catalyst facilitated by the exposure to excessively high temperatures of the reaction heat.

In such a multitubular reactor, a fluid for cooling (hereinafter, also referred to as a heat medium) is circulated outside a reaction tube assembly (i.e. on the side of a shell) to maintain the temperature necessary for the reaction, while heat exchange between a process fluid (in the case of reaction of vapor phase catalytic oxidation, a process gas) and the heat medium is simultaneously conducted as performed in heat exchangers widely used in chemical plants. This process prevents the catalyst in the tube from deteriorating owing to the excessive local temperature rise in catalyst layer (the formation of hot spots).

However, the heat of reaction from the reaction of vapor phase catalytic oxidation is so large as to cause the deterioration of the catalyst due to the frequent occurrence of hot spots and to cause a runaway reaction by exceeding the allowable temperature of the catalyst. This can result in problems such as inability to utilize the catalyst.

Numerous methods of restraining the formation of hot spots in a multitubular reactor used for a reaction of vapor phase catalytic oxidation have been proposed. In a method disclosed, for example, in JP 08-92147 A, the direction of flow of a heat medium within a reactor shell and the direction of flow of a raw material gas directed by the reactor are made parallel. In addition, the flow of the heat medium is meandered with baffles to move upward. Thereby, the temperature of the heat medium is rendered uniform with a 2–10° C. or less temperature difference from the inlet to the outlet. However, the method pays attention to only the temperature difference of heat medium. Thus, in an actual reactor having an uneven heat transfer coefficient therein, the method poses a disadvantage of generating hot spots in an area with a poor heat transfer coefficient.

JP 2000-93784 A has proposed a method of restraining the formation of hot spots in which the flows of reacted raw material gas and a heat medium are made downward parallel to prevent the gas accumulation containing no heat medium. It has further described a method of making only the catalyst around the entry of catalyst layer which is most easily deteriorated exchangeable by supplying raw material gas into the reactor via the upper portion thereof to pass downward through the catalyst layer of the reaction tube. However, the method focuses on the relationship of raw material gas flow with the heat medium. Thus, it has a disadvantage of insufficiently removing the heat of reaction to generate hot spots if the flow velocity of the heat medium and the heat transfer coefficient are low.

Alternatively, JP 2001-137689 A has proposed a method of restraining the formation of hot spots by defining how baffles, which change the direction of heat medium flow, and reaction tubes are placed. In the multitubular reactor, a heat medium for cooling the heat of reaction is circulated on the side of shell thereof. Owing to the existence of the reaction tube assembly and the baffles in a flow path on the side of shell, the heat medium flows separately into the reaction tube assembly, into a space between the baffles and the reaction tube assembly, and into a space between the baffles and the reactor body. However, the heat medium passing through the portion other than the reaction tube assembly is not useful for cooling the reaction tubes, and thus the amount of such a medium should be reduced as much as possible. Also, JP 2001-137689 A has a description relating to the flow rate of all heat media but has no description relating to a heat transfer coefficient. Therefore, the problems such as hot spots must have been alleviated by taking the heat transfer coefficient into consideration.

In a multitubular reactor, the heat of reaction which occurs within reaction tubes is removed by the circulation of a heat medium. Thus, if the heat of reaction is not effectively removed, hot spots are formed in a catalyst layer, resulting in the reduction in the yield of a desired product, the deterioration of catalytic activity, and the like.

The temperature distribution of the catalyst layer is determined by the balance between the amount of heat generation within the reaction tube and the amount of heat transfer to the heat medium. Accordingly, the approach to decrease the temperature in hot spots has been attempted in which the heat transfer coefficient on the side of the heat medium is increased by giving the larger flow rate of the heat medium. However, augmenting the flow rate of the heat medium more than necessary causes the increase in size of a circulation pump for the heat medium. Moreover, the larger power for driving the circulation pump for the heat medium is required, resulting in a problem in that an operation cost increases.

DISCLOSURE OF THE INVENTION

Thus, an object of the present invention is to provide a method of vapor phase catalytic oxidation using a multitubular reactor, which is capable of: effectively removing the heat of reaction with the appropriate amount of circulation of a heat medium maintained; preventing the formation of hot spots; efficiently providing a desired product; and extending the lifetime of a catalyst without the deterioration of catalytic activity.

The inventors of the present invention have conducted the various studies for attaining the above object and have analyzed the flow and heat transfer of a heat medium on the side of shell of a multitubular reactor which is increased in size. As a result, they have found that a method of vapor phase catalytic oxidation for attaining the above object can be provided by performing a reaction of vapor phase catalytic oxidation under such conditions that the heat transfer coefficient of a heat medium is a particular value, and have completed the present invention.

That is, the present invention is as follows.

(1) A method of a vapor phase catalytic oxidation of a substance to be oxidized with a gas containing molecular oxygen by means of a multitubular reactor, the multitubular reactor comprising: a cylindrical reactor shell fitted with a raw material supply port and a product outlet; multiple circular conduits disposed around the cylindrical reactor shell and used to introduce a heat medium into the cylindrical reactor shell or to lead the heat medium out therefrom; a circulation device for connecting the multiple circular conduits to each other; multiple reaction tubes restrained by means of multiple tube plates of the reactor and having a catalyst accommodated therein; and multiple baffles arranged in the longitudinal direction of the reaction tube and used to change a direction of the heat medium introduced into the reactor shell, wherein the method comprises: performing a reaction of vapor phase catalytic oxidation under such conditions that the heat transfer coefficient of the heat medium is 1,000 W/(m$^2$·K) or higher.

(2) The method of vapor phase catalytic oxidation according to (1), wherein the method comprises: oxidizing propylene, propane, or isobutylene with molecular oxygen to produce (meth)acrolein; and/or oxidizing (meth)acrolein with molecular oxygen to produce (meth)acrylic acid.

BEST MODE FOR CARRYING OUT THE INVENTION

Figure 1:
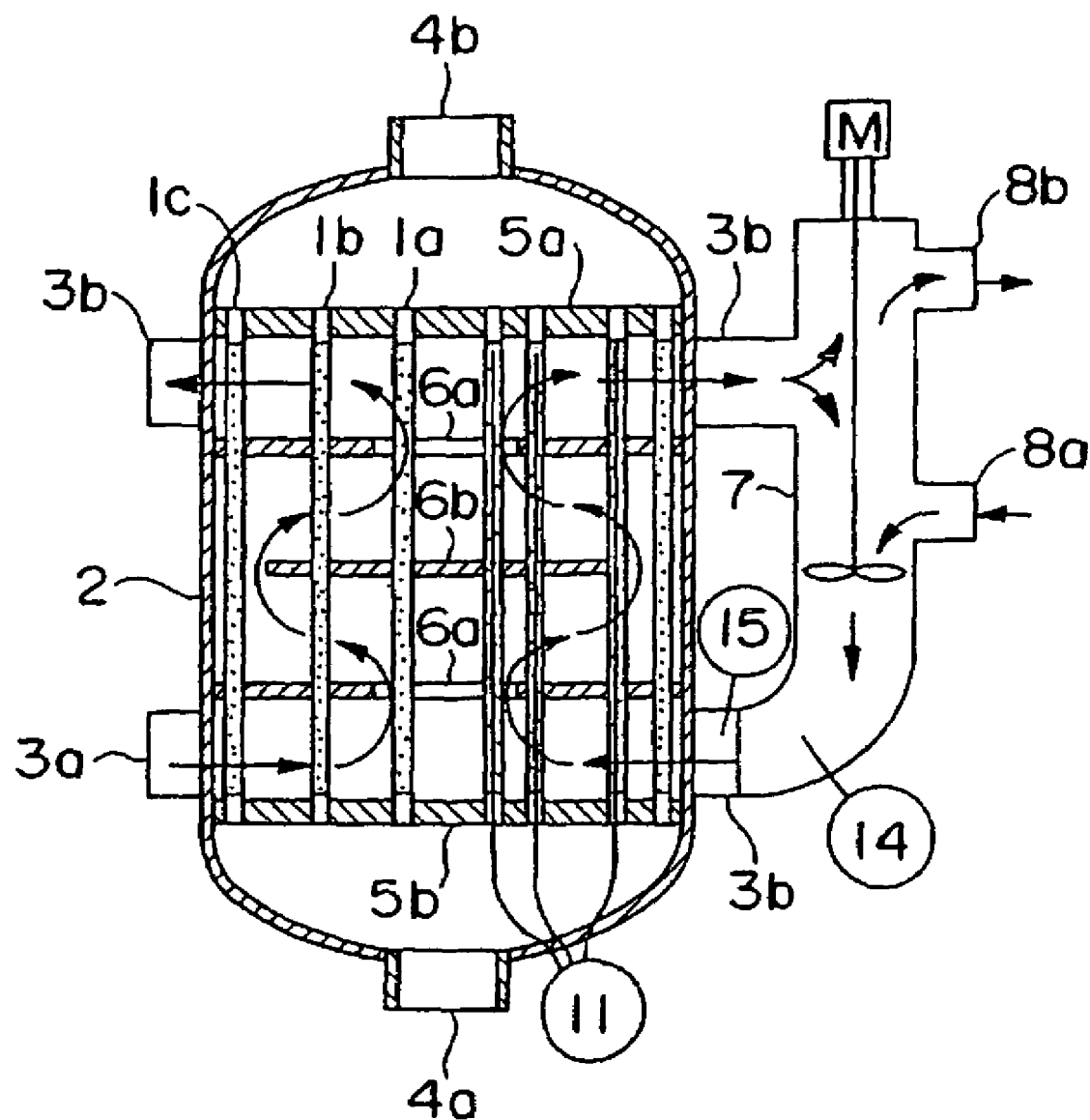
FIG. 1 is one embodiment of a multitubular heat-exchange reactor used in a method of vapor phase catalytic oxidation of the present invention.

Hereinafter, the present invention is described in detail.

The present invention provides a method of a vapor phase catalytic oxidation of a substance to be oxidized with a gas containing molecular oxygen by means of a multitubular reactor comprising: a cylindrical reactor shell fitted with a raw material supply port and a product outlet; multiple circular conduits disposed around the cylindrical reactor shell and used to introduce a heat medium into the cylindrical reactor shell or to lead the heat medium out therefrom; a circulation device for connecting the multiple circular conduits to each other; multiple reaction tubes restrained by means of multiple tube plates of the reactor and having a catalyst accommodated therein; and multiple baffles arranged in the longitudinal direction of the reaction tube and used to change the direction of the heat medium introduced in the reactor shell, the method being characterized in that the reaction of vapor phase catalytic oxidation is performed under such conditions that the heat transfer coefficient of the heat medium is 1,000 W/(m$^2$/K) or more.

In the present invention, benzene or butane is used as a substance to be oxidized and subjected to vapor phase catalytic oxidation with a gas containing molecular oxygen to produce maleic anhydride. The invention is also utilized when at least one of xylene and naphthalene is used as a substance to be oxidized and subjected to vapor phase catalytic oxidation with a gas containing molecular oxygen to produce phthalic anhydride.

More preferably, in the present invention, propylene, propane, or isobutylene is used as a substance to be oxidized and subjected to vapor phase catalytic oxidation with a gas containing molecular oxygen to produce (meth)acrolein (hereinafter, also referred to as a preliminary stage (a first stage) reaction). The (meth)acrolein produced in the preliminary stage reaction is then used as a substance to be oxidized and subjected to vapor phase catalytic oxidation with a gas containing molecular oxygen to produce (meth) acrylic acid (hereinafter, also referred to as a subsequent stage (a second stage) reaction).

In the present invention, the heat transfer coefficient of a heat medium is determined, in particular by means of the flow analysis of the heat medium using simulation analysis with a computer.

The above flow analysis of the heat medium can be performed by simulating: the defined structure of the reactor such as the layout of baffles and of reaction tubes and a heat medium supply port; and defined items on the heat medium such as physical properties and a flow rate thereof. More particularly, the flow direction and flow velocity of the heat medium are determined through calculation by using equations of conservation of momentum, conservation of mass, and conservation of enthalpy etc. In the present invention, the analysis can be conducted using a CFX (manufactured by AEA Technology Plc) as fluid analysis software.

Consequently, the above fluid analysis of the heat medium allows a portion having a low heat transfer coefficient of the heat medium to be detected.

In addition, in the present invention, the reaction of vapor phase catalytic oxidation is carried out under such conditions that the heat transfer coefficient of the heat medium is 1,000 W/(m$^2$/K) or more. In particular, a reaction tube in an area having a heat transfer coefficient of less than 1,000 W/(m$^2$/K) is sealed so as not to leak a gas therefrom, or a reaction is not allowed to occur by filling no catalyst into the reaction tube. Alternatively, the reaction tube itself is not provided in such an area. This can prevent an abnormal reaction caused by an excessively increased temperature in a reaction tube in an area having a low heat transfer coefficient of the heat medium.

Also, a space between baffles disposed on the side of reactor shell where a heat medium flows and a reactor body, or a space between the baffles and the reaction tube is made narrower or is provided with a patch to reduce the amount of the heat medium leaked from the space. Thus, the heat medium can have an increased heat transfer coefficient. Alternatively, the reaction of vapor phase catalytic oxidation can be performed by increasing the flow rate of the heat medium or changing the size of a baffle to remove an area having a heat transfer coefficient of the heat medium of less than 1,000 W/(m$^2$/k).

FIG. 1 shows a first embodiment of a multitubular heat-exchange reactor, which is used in the method of vapor phase catalytic oxidation of the present invention.

In a shell 2 of the multitubular reactor, reaction tubes 1a, 1b, and 1c are arranged by fixing the tubes on tube plates 5a, 5b, respectively. A raw material supply port as an inlet of the reaction raw material gas, and a product outlet as an outlet of the products are represented by reference numerals 4a and 4b. However, the flow of gas may be in any of directions. On the outer periphery of the reactor shell, a circular conduit 3a used for the introduction of a heat medium is disposed. The heat medium pressurized by a circulation pump 7 for the heat medium moves up in the reactor shell through the circular conduit 3a and returns to the circulation pump through a circulation conduit 3b as the direction of flow is changed. This is because of an alternative arrangement of: hollow baffles 6a having their respective openings near the central part of the reactor shell; and hollow baffles 6b disposed such that openings are formed between the respective hollow baffles 6b and the outer periphery of the reaction shell. Part of the heat medium absorbing the heat of reaction is cooled by a heat exchanger (not shown in the figure) via an exhaust tube disposed on the upper part of the circulation pump 7 and then reintroduced into the reactor through a heat medium supplying line 8a. The temperature of the heat medium is controlled by controlling the temperature or flow rate of a reflux heat medium introduced from the heat medium supplying line 8a in response to an instruction from a thermometer 14.

Although the temperature control of the heat medium depends on the performance of a catalyst used, it is preferable to carry out the temperature control such that a temperature difference between the heat medium in the heat medium supplying line 8a and the heat medium in a heat medium extraction line 8b is 1 to 10° C., preferably 2 to 6° C.

Current plates (not shown in the figure) are preferably disposed on shall plates on the inside of the respective circular conduits 3a and 3b to minimize the distribution of the flow rate of the heat medium in a circumferential direction. A perforated plate or a plate having a slit is used as a current plate. The flow is rectified so that the opening area of the perforated plate or a slit-spacing may be changed to allow the heat medium to be introduced at a constant flow rate from the entire periphery. The inner temperature of the circular conduit (3a, or preferably together with 3b) can be observed by providing two or more thermometers 15.

The number of the baffles disposed in the reaction shell is preferably three (two 6a type baffles and one 6b type baffle) or more, but is not particularly limited. Hereinafter, a description will be made while a reactor (FIG. 1) having three baffles is taken as an example.

The presence of the baffles prevents the heat medium from flowing upward and changes the flow direction of the heat medium in the lateral direction with respect to the axial direction of the reaction tube. Therefore, the heat medium is concentrated into the central part from the outer periphery of the reactor shell and then turns around at the opening of the baffle 6a to direct to the outer periphery, followed by reaching the external cylinder of the shell. The heat medium turns around at the outer periphery of the baffle 6b again and is concentrated into the central part and moves up through the opening of the baffle 6a to the outer periphery along a top tube plate 5a of the reactor shell, followed by circulating the pump via the circular conduit 3b.

In addition, the baffles 6a and 6b have holes for putting the reaction tubes therethrough and spaces between the baffles and the shell against thermal expansion of the reactor. Therefore, a certain amount of the heat medium may pass through those holes and spaces to cause a side stream. As the side stream does not effectively contribute to the removal of reaction heat, lessening the side stream is desirable.

A thermometer 11 is inserted into a reaction tube disposed inside the reactor and a signal from the thermometer 11 can be transmitted to the outside of the reactor to record a temperature distribution in the axial direction of the reactor in the catalyst layer. Two or more thermometers may be inserted into the reaction tubes to measure the temperatures generally at 3 to 20 points per thermometer in the axial direction of the reaction tube.

The reaction tubes can be grouped into three types with respect to their arrangements on the basis of the relationship between the reaction tubes and the openings of three baffles, i.e., the relationship between the reaction tubes and the flow direction of the heat medium.

The reaction tube 1a is restrained only by the baffle 6b but not restrained by two baffles 6a because the reaction tube 1a is disposed in the openings of the baffles 6a. The reaction tube 1a is disposed in an area where the heat medium passing through the outside of the reaction tube turns around at the central part of the reactor. The flow of the heat medium is principally in parallel to the axial direction of the reaction tube. The reaction tube 1b is restrained by three baffles 6a, 6b, 6a and most reaction tubes are disposed in this area. In relation to the reaction tubes, the flow direction of the heat medium is almost perpendicular to the axial direction of the reaction tube in the entire area of the reaction tube. The reaction tube 1c is in the vicinity of the outer periphery of the reactor shell and positioned at the outer periphery of the baffle 6b without being restrained by the baffle 6b. At the central part of the reaction tube 1c, the reaction tube 1c is in an area where the heat medium turns around. In the region, i.e., the central part of the reaction tube, the heat medium flows in parallel to the axial direction of the reaction tube.

Figure 4:
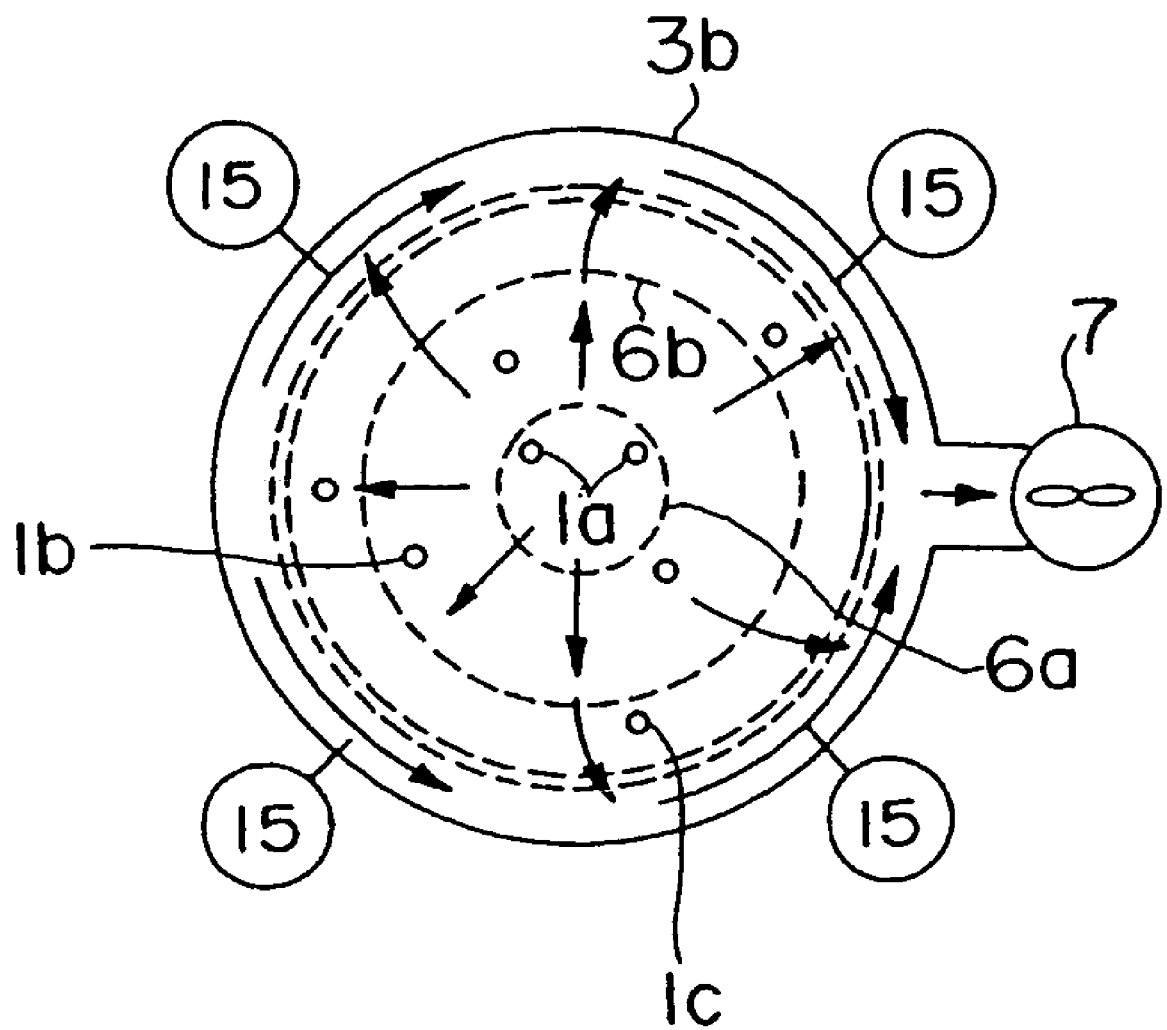
FIG. 4 is a top view of the multitubular reactor according to the present invention.

FIG. 4 shows a top view of the reactor of FIG. 1. The central and edge parts of the reactor shell correspond to an area where the heat medium is concentrated by the openings of the baffles 6a and 6b and the reaction tubes 1a and 1c are disposed. Therefore, the area not only allows the flow of the heat medium to be in parallel to the axes of the respective tubes but also allows the flow rate of the heat medium to be extremely low. In the area, therefore, the heat transfer coefficient of the heat medium tends to be low.

Figure 2:
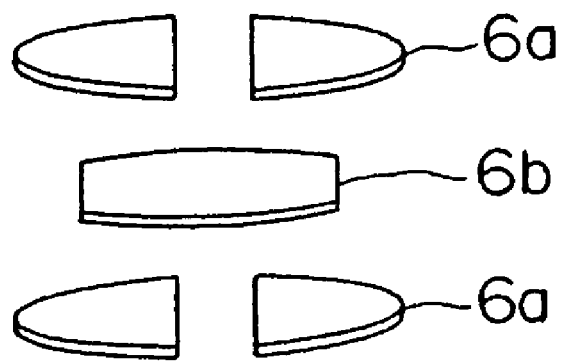
FIG. 2 is one embodiment of baffles used in a multitubular reactor according to the present invention.
Figure 3:
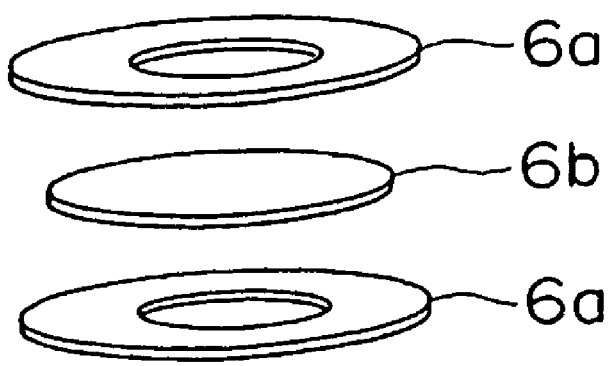
FIG. 3 is one embodiment of baffles used in the multitubular reactor according to the present invention.

Regarding baffles used in the present invention, the baffle 6a has an opening in the vicinity of the central part of the reactor shell. Also, the baffle 6b is opened between the outer periphery and an external cylinder of the shell. As far as the heat medium can turn around at each opening, can be prevented from causing a by-pass flow thereof, and can change the flow rate, any of baffles, such as a segment-type noncircular baffle shown in FIG. 2 and a disk-type baffle shown in FIG. 3, can be applied. Both types of the baffles do not affect the relationship between the flow direction of the heat medium and the axis of the reaction tube.

In particular, the disk-type baffle is used as a common baffle more than the other. The central-part opening area of the baffle 6a is preferably 5 to 50%, more preferably 10 to 30% of the cross-sectional area of the reactor shell. The opening area between the baffle 6b and the reactor shell plate 2 is preferably 5 to 50%, more preferably 10 to 30% of the cross-sectional area of the reactor shell. If the opening ratio between the baffles (6a and 6b) is too small, an increase in pressure loss between the circular conduits (3a and 3b) occurs as the flow path of the heat medium extends, resulting in an increase in power required for the heat medium circulation pump 7. If the opening ratio between the baffles is too large, in general, there is an increase in number of the reaction tubes (1a and 1c) disposed in an area where the heat transfer coefficient of the heat medium tends to be low.

In most cases, the distances between the baffles disposed (the distance between the baffles 6a and 6b and the distances between the baffle 6a and the tube plates 5a, 5b) are equal to each other. However, there is no need to make them equal. The distances may be defined to ensure a required flow rate of the heat medium to be defined by the heat of oxidation reaction caused in the reaction tube, while minimizing a pressure loss of the heat medium. In addition, it is preferable to avoid that the position of the baffle corresponds to the temperature peak position which indicates the highest temperature among the distribution of temperatures represented by the catalyst layers in the reaction tube. The heat transfer coefficient is low near the surface of the baffle because the flow rate of the heat medium near the surface of the baffle decreases. Thus, when the position of the baffle corresponds to the position of the temperature peak, a further increase in temperature of such a portion occurs.

For preventing the correspondence of the temperature peak position and the baffle position, it is possible to consider using the computer simulation described above.

A mixture gas of water vapor with propylene, propane, isobutylene, and/or (meth)acrolein, and a gas containing molecular oxygen is introduced as a raw material gas in the multitubular reactor in the present invention.

The concentration of propylene, propane, or isobutylene in the raw material gas is 3 to 15 vol %. The concentration of oxygen is 1.5 to 2.5 mole times, and the concentration of water vapor is 0.8 to 2 mole times as high as that of propylene, propane, or isobutylene.

The introduced raw material gas is divided into the respective reaction tubes $1a$, $1b$, $1c$, and so on and then passes through the reaction tubes to carry out a reaction under an oxidation catalyst included in each of the reaction tubes.

The catalysts to be used in the vapor phase catalytic oxidation reaction of the present invention, for example, catalysts used for the oxidation of propylene, propane, or isobutylene and for the oxidation of (meth)acrolein have only to be catalysts generally used, and examples thereof include catalyst systems containing Mo, Bi, Sb, and so on.

It is preferable to fill the reaction tube with the catalyst after changing the activity of the catalyst to prevent the generation of hot spots and the heat accumulation in the hot spots. There are many methods of changing the activity of a catalyst in the reaction tube. Concretely, the methods include one using different types of the catalysts and one involving adjusting the activity of the catalyst by mixing and diluting the catalyst with an inactive substance. For instance, the raw material gas inlet part of the reaction tube can be filled with a catalyst having a high inactive substance rate, while the outlet part of the reaction tube can be filled with a catalyst having a low inactive substance rate or a undiluted catalyst.

In addition, the activity of the catalyst may be changed every reaction tube in addition to a change in activity of the catalyst in a single reaction tube.

The degrees of dilution of the catalysts in all of the reaction tubes should not be made equal to each other. For instance, the reaction tube $1a$ located at the central part of the reactor shell has a higher peak temperature (a part having the highest temperature of the catalyst layer in the reaction tube). For avoiding this phenomenon, the ratio of an inactive substance may be increased more than other reaction tubes ($1b$, $1c$) located at the other parts. Therefore, it is preferable that the degree of dilution of a catalyst for each reaction tube be changed to adjust the conversion ratios of all of the reaction tubes to the same level.

An inactive substance used in the present invention is not particularly limited as far as it is a material which is stable under reaction conditions and shows no reactivity with a raw material and a product. Concretely, however, the inactive substances may be those used as carriers for catalysts such as alumina, silicon carbide, silica, zirconia oxide, and titanium oxide. In addition, just as in the case of the catalyst, the form of the carrier is not limited. The form may be, for example, any of globular, cylindrical, ring, and infinite forms. In addition, the dimensions of the carrier may be defined in consideration of the diameter of the reaction tube and the differential pressure.

In most cases, Niter which is a mixture of nitrates is used as a heat medium that flows to the shell side of the reactor. Besides, any of organic-fluid phenyl ether-based heat media may be used. The flow of the heat medium removes the heat of reaction from the reaction tube. However, a heat medium introduced in the reactor shell from the circular conduit $3a$ for the induction of a heat medium has an area where the heat medium flows from the outer periphery of the reactor to the central part and an area where the heat medium turns around at the central part. When the direction of the heat medium is perpendicular to the axis of the reaction tube, the heat transfer coefficient is generally 1,000 to 2,000 $W/(m^2 \cdot K)$. When Niter is used as a heat medium, the heat transfer coefficient may be 100 to 300 $W/(m^2 \cdot K)$ even though the value depends on the flow rate, upward flow or downward flow of the heat medium when the flow is not perpendicular to the axis.

On the other hand, the heat transfer coefficient of the catalyst layer in the reaction tube is almost 100 $W/(m^2 \cdot K)$, even though it depends surely on the flow rate of the raw material gas. When the flow of the heat medium is perpendicular to the axis of the reaction tube, the heat transfer coefficient of the heat medium outside the tube is 10 to 20 times as high as the heat transfer coefficient of the catalyst layer in the tube. Therefore, a change in the flow rate of the heat medium exerts a little effect on the general heat transfer coefficient (here, the general heat transfer coefficient means a heat transfer coefficient calculated in consideration of various conditions including the heat transfer coefficient of the heat medium outside the reaction tube, the heat transfer coefficient of the catalyst layer in the reaction tube, the heat conductivity of the reaction tube, and the thickness of the reaction tube). However, when the heat medium flows in parallel to the axis of the tube, the heat transfer coefficients for the outside and inside of the reaction tube are almost equal to each other. Thus, the efficiency of heat removal may be extensively influenced by the fluid state of the heat medium outside the reaction tube. That is, when the heat transfer coefficient of the heat medium outside the tube is 100 $W/(m^2 \cdot K)$, the general heat transfer coefficient of the heat medium is almost half of the case of 1,000 to 2,000 $W/(m^2 \cdot K)$. A decrease in heat transfer coefficient of the heat medium outside the tube exerts a large influence on the general heat transfer coefficient. Therefore, while considering the heat transfer coefficients of the outside and inside of the reaction tube, the conditions for carrying out a vapor phase catalytic oxidation reaction should be studied.

The inner diameter of the reaction tube of the multitubular reactor of the present invention is preferably 10 to 50 mm, more preferably 20 to 30 mm, even though it is influenced by the amount of the heat of reaction in the reaction tube and the particle size of the catalyst. If the inner diameter of the reaction tube is too small, the amount of the catalyst filled decreases. Thus, the number of the reaction tubes increases with respect to the amount of the catalyst required, resulting in an increase in size of the reactor. On the other hand, if the inner diameter of the reaction tube is too large, the surface area of the reaction tube decreases with respect to the amount of the catalyst required. Therefore, the heat transfer area for removing the heat of reaction decreases.

Figure 5:
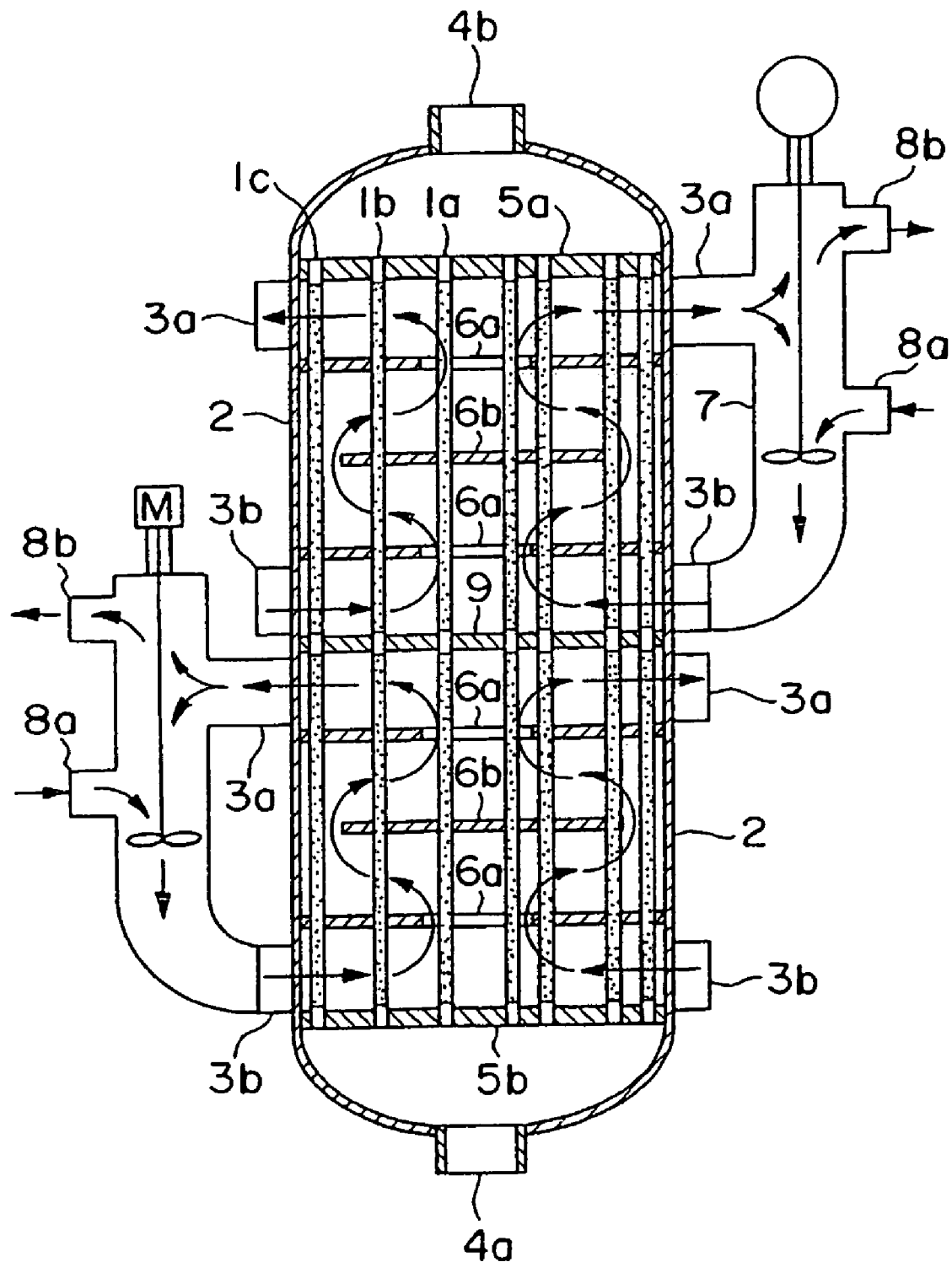
FIG. 5 is one embodiment of a multitubular heat-exchange reactor used in the method of vapor phase catalytic oxidation of the present invention.

FIG. 5 shows a multitubular reactor having a reactor shell divided by an intermediate tube plate 9 and a method using such a reactor is also comprehended in the method of vapor phase catalytic oxidation according to the present invention. Different heat media circulate through the respective divided spaces, and temperatures of the media are controlled at different temperatures. A raw material gas may be introduced from either 4a or 4b. The raw material gas introduced from a raw material supply port reacts successively in reaction tubes in the reactor.

In the multitubular reactor shown in FIG. 5, upper and lower areas of the reactor divided by the intermediate tube plate 9 contain a heat media at different temperatures. Therefore, there are different cases:

1) the same catalyst fills throughout a reaction tube, while the reactions are allowed at different temperatures in raw material gas inlet and outlet parts, respectively;

2) a catalyst fills the inlet part for a raw material gas, while no catalyst fills the outlet part such that the outlet part remains as an empty tube or the outlet part is filled with an inactive material with no reaction activity to cool a reaction product rapidly;

3) different catalysts fill the raw material gas inlet and outlet parts, respectively, and no catalyst fills a part between the inlet and outlet parts such that the part remains as an empty tube or the part is filled with an inactive material with no reaction activity to cool a reaction product rapidly.

For example, a gas mixture of a gas containing molecular oxygen with propylene, propane, or isobutylene may be introduced from the raw material supply port into the multitubular reactor of FIG. 5 to be used in the present invention, to produce (meth)acrolein at first in a preliminary stage part for an early stage reaction. The (meth)acrolein is then oxidized in a second stage part for a subsequent stage reaction to produce (meth)acrylic acid. The first stage part and the second stage part in the reaction tube have different catalysts, respectively. Those first and second stage parts are controlled at different temperatures to carry out the reactions under optimal conditions. A part between the preliminary stage part and the subsequent stage part of the reaction tube, where the intermediate tube plate locates, is preferably filled with an inactive material that is not involved in the reaction.

Figure 6:
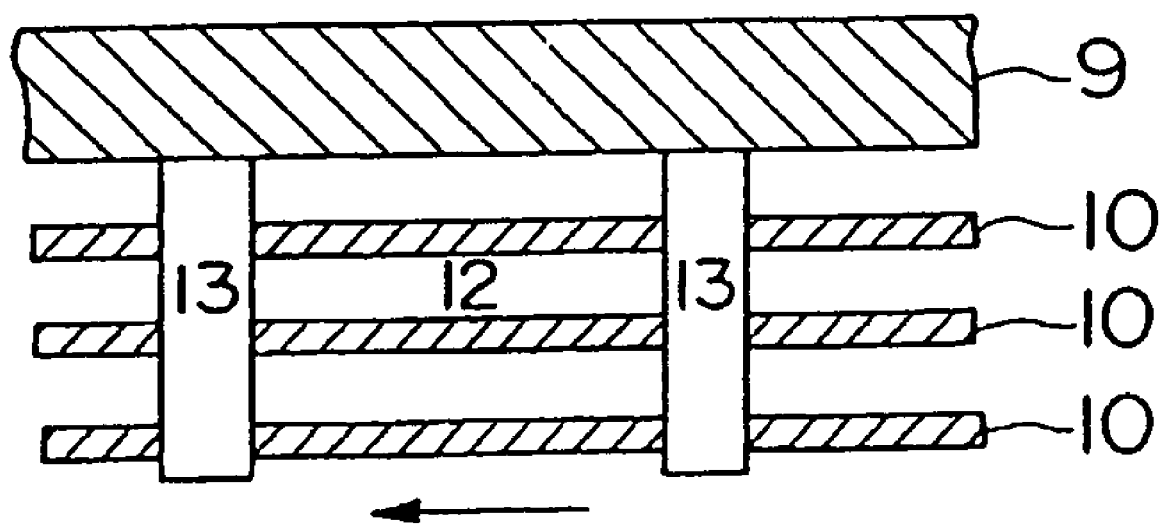
FIG. 6 is an enlarged view of an intermediate tube plate which separates a shell of the multitubular reactor of FIG. 5.

FIG. 6 shows an enlarged view of the intermediate tube plate. Though the preliminary stage part and the subsequent stage part are controlled at different temperatures, when the temperature differences exceed 100° C., heat transfer from the high temperature heat medium to the low temperature heat medium becomes too large to be ignored and the accuracy of the reaction temperature at low temperatures tends to be low. In such a case, insulation is necessary to prevent heat transfer above or under the intermediate tube plate. FIG. 6 shows the use of insulating plates. An insulating effect is preferably obtained by installing two or three heat shield plates 10 at the positions about 10 cm above or below the intermediate tube plate to form a stagnant space 12 that is filled with the heat medium but has no flow. The heat shield plate 10 may be fixed to the intermediate tube plate 9 with, for example, a spacer rod 13.

Although arrows in FIGS. 1 and 5 indicate that the flow direction of a heat medium in the reactor shell is an upward direction, the flow directions may be in the opposite direction in the present invention. Decision on the directions of heat medium circulation flow should be made to avoid a phenomenon of entrainment in which the heat medium flow entrains gases, particularly inactive gases such as nitrogen, which may be present on top of the reactor shell 2 and of the circulation pump 7. When the heat medium has an upflow (FIG. 1), a phenomenon of cavitation may be caused by entrainment of gas in the upper part in the circulation pump 7, and the pump is broken down in the worst cases. When the heat medium has a downflow, the phenomenon of gas entrainment may occur in the upper part of the reactor shell to produce retention parts in gas phase in the upper part of the shell. Upper parts of reaction tubes around which the gas retention parts are located will not be cooled by the heat medium.

As a prevention plan against such gas-retention, it is necessary to install an gas extraction line to substitute gases in gas layers with the heat medium. For the purpose, the pressure in the shell should be brought high by raising the heat medium pressure in a heat-medium supply line 8a, and by installing a heat-medium extraction line 8b as high as possible. It is preferable to install the heat-medium extraction line at least higher than the tube plate 5a.

When the multitubular reactor shown in FIG. 1 is adopted as a multitubular reactor to oxidize propylene, propane, or isobutylene with a gas containing molecular oxygen, and used with downflows of the process gas, in other words, when the raw material gas enters from 4b and the product exits from 4a, the concentration of the target product (meth) acrolein is high in the vicinity of the product outlet 4a in the reactor. In this case, the temperature of the process gas becomes also high owing to heat of the reaction. Thus, in this case, it is preferable to have the process gas cooled down sufficiently by installing a heat exchanger after 4a in the reactor of FIG. 1 to prevent (meth)acrolein from an autoxidation reaction (autolysis reaction).

When the multitubular reactor shown in FIG. 5 is adopted with downflows of the process gas, in other words, when the raw material gas enters from 4b and the product exits from 4a, the concentration of the target product (meth)acrolein is high in the vicinity of the intermediate tube plate 9, which is the reaction end point in the first stage. Therefore, the temperature of the process gas near the intermediate tube plate becomes also high owing to heat of the reaction. When only the first stage (5a-6a-6b-6a-9) contains a catalyst, the reaction tube 1a, 1b, and 1c in the second stage (from 9 to 5b) is kept away from the reaction and the process gas is cooled down with a heat medium flowing in the conduits on the shell side to prevent (meth)acrolein from autoxidation reaction. In this case, the reaction tubes 1a, 1b, and 1c (from 9 to 5b) are retained without any catalyst to be empty or are filled with a solid material with no reaction activity. The latter is preferable to improve properties in heat transfer.

When different catalysts are filled to the first stage (5a-6a-6b-6a-9) and to the second stage (9-6a'-6b'-6a'-5b) of the multitubular reactor shown in FIG. 5 to produce (meth) acrolein from propylene, propane, or isobutylene in the first stage and to produce (meth)acrylic acid in the second stage, the temperature of the catalyst layer in the first stage becomes higher than the temperature of the catalyst layer in the second stage. Specifically, since the temperature becomes high in the vicinity of the reaction end point in the first stage (6a-9) and in the vicinity of the reaction initiation point in the second stage (9-6a'), it is preferable that the reaction is not carried out at this part and the process gas be cooled down with a heat medium flowing in the conduits on the shell side to prevent (meth)acrolein from autoxidation reaction. In this case, parts without any catalyst are to be arranged in the vicinity of the intermediate tube plate 9 (between 6a-9-6a' of the reaction tubes 1a, 1b and 1c) to be empty or the vicinity is filled with a solid material with no reaction activity. The latter is preferable to improve properties in heat transfer.

EXAMPLES

Hereinafter, the present invention is described concretely with reference to examples. It is needless to say that the present invention is not only limited to these examples.

Example 1

To prepare for performing an oxidation reaction of propylene, catalyst powder having a composition of Mo(12)Bi(5)Ni(3)Co(2)Fe(0.4)Na(0.2)B(0.4)K(0.1)Si(24)O(x) was produced as the preliminary stage catalyst (Composition x of oxygen is a value determined by the oxidation state of each metal). A ring catalyst with an outside diameter of 5 mm Ø, an inside diameter of 2 mm Ø, and a height of 4 mm was molded from the catalyst powder and used.

A reactor shown in FIG. 1 was used, in which the reactor had a reactor shell with an inside diameter of 4,500 mm having 12,000 reaction tubes made of stainless steel, each of the reaction tubes having a length of 3.5 m, an inside diameter of 24 mm Ø, and an outside diameter of 28 mm Ø.

Niter, a molten salt of nitrate mixture, was used as a heat medium and supplied from a lower part of the reactor.

The heat medium temperature indicates the temperature of the heat medium supplied to the reactor. The reactor was operated with a heat medium flow rate of 2,500 m$^3$/hr.

Fluid analysis simulation of the heat medium was performed using fluid analysis software CFX4 (manufactured by AEA Technology Plc) based on the conditions such as the size and arrangement of the reaction tubes, the flow rates of the feed gas, and the flow rate of the heat medium. The result showed the presence of an area with a heat transfer coefficient of 500 to 900 W/(m$^2$·K) in the central part of the reactor and the other parts with heat transfer coefficient of 1,000 to 1,600 W/(m$^2$·K).

Each reaction tube in an area with a heat transfer coefficient of 500 to 900 W/(m$^2$·K) was closed with a metal lid to prevent a gas from flowing.

Each of the rest of the reaction tubes was filled with 1.5 L of the preliminary stage catalyst described above.

A raw material gas containing propylene at 9 vol % in concentration was supplied from the top of the reactor at a gauge pressure of 75 kPa. Temperature distributions in the reaction tubes were measured by inserting the thermometer having 10 measuring points in the axial directions of the tubes. In particular, the highest temperature was indicated as the peak temperature.

With one week of the operation at 330° C. in heat medium temperature, the propylene conversion was 97%, the combined yield of acrolein and acrylic acid was 92%, and the peak temperature in the reaction catalyst layers was 385° C.

Comparative Example 1

The metal lids were removed from the reaction tubes in the area with a low heat transfer coefficients of 500 to 900 W/(m$^2$K) in Example 1. The test was conducted under the same conditions as those of Example 1 except that each of the reaction tubes in this area was also filled with 1.5 L of the same preliminary stage catalyst as that used in Example 1.

A raw material gas containing propylene at 9 vol % in concentration was supplied from the top of the reactor at a gauge pressure of 75 kPa. Temperature distributions in the reaction tubes were measured by inserting the thermometer having 10 measuring points in the axial directions of the tubes.

With one week of the operation at 330° C. in heat medium temperature, the propylene conversion was 95%, the combined yield of acrolein and acrylic acid was 89%, and the peak temperature in the reaction catalyst layers was 430° C. in the reactor central part, and 385° C. in the other parts.

INDUSTRIAL APPLICABILITY

According to the present invention, by performing the vapor phase catalytic oxidation in the conditions with heat transfer coefficients of 1,000 W/(m$^2$·K) or higher, there is provided the method of vapor phase catalytic oxidation using a multitubular reactor, which is capable of: efficiently removing heat of reaction; preventing the formation of hot spots; efficiently providing a desired product; and extending the lifetime of a catalyst without the deterioration of catalytic activity.

The invention claimed is:

1. A method of a vapor phase catalytic oxidation of a substance to be oxidized with a gas containing molecular oxygen by means of a multitubular reactor, the multitubular reactor comprising: a cylindrical reactor shell fitted with a raw material supply port and a product outlet; multiple circular conduits disposed around the cylindrical reactor shell and used to introduce a heat medium into the cylindrical reactor shell or to lead the heat medium out therefrom; a circulation device for connecting the multiple circular conduits to each other; multiple reaction tubes restrained by means of multiple tube plates of the reactor and having a catalyst accommodated therein; and multiple baffles arranged in a longitudinal direction of the reaction tube and used to change a direction of the heat medium introduced into the reactor shell, wherein the method comprises:

performing a reaction of vapor phase catalytic oxidation under such conditions that a heat transfer coefficient of the heat medium is 1,000 W/(m$^2$·K) or higher, and preventing the reaction of vapor phase catalytic oxidation in an area of the reactor having a heat transfer coefficient of the heat medium less than 1,000 W/(m$^2$·K).

2. The method of vapor phase catalytic oxidation according to claim 1, wherein the method comprises:

oxidizing propylene, propane, or isobutylene with molecular oxygen to produce (meth)acrolein; and/or oxidizing (meth)acrolein with molecular oxygen to produce (meth)acrylic acid.

* * * * *